(12) United States Patent
Kirsch et al.

(10) Patent No.: US 9,034,011 B2
(45) Date of Patent: May 19, 2015

(54) ANCHORING DEVICE

(75) Inventors: David Kirsch, Madison, CT (US);
Michael Primavera, Orange, CT (US);
Ahmad Robert Hadba, Middlefield, CT (US); Gerald Hodgkinson, Guilford, CT (US); Timothy D. Kosa, Hamden, CT (US); Nicholas Maiorino, Branford, CT (US)

(73) Assignee: Covidien LP, Mansfield, MA (US)

( * ) Notice: Subject to any disclaimer, the term of this patent is extended or adjusted under 35 U.S.C. 154(b) by 682 days.

(21) Appl. No.: 12/783,977

(22) Filed: May 20, 2010

(65) Prior Publication Data

US 2010/0268272 A1 Oct. 21, 2010

Related U.S. Application Data

(63) Continuation-in-part of application No. 12/416,421, filed on Apr. 1, 2009, which is a continuation-in-part of application No. 12/362,002, filed on Jan. 29, 2009.

(60) Provisional application No. 61/041,302, filed on Apr. 1, 2008.

(51) Int. Cl.
*A61B 17/04* (2006.01)
*A61B 17/06* (2006.01)
*A61B 17/00* (2006.01)

(52) U.S. Cl.
CPC ........ *A61B 17/0401* (2013.01); *A61B 17/06166* (2013.01); *A61B 2017/00867* (2013.01); *A61B 2017/00871* (2013.01); *A61B 2017/0404* (2013.01); *A61B 2017/0406* (2013.01);
(Continued)

(58) Field of Classification Search
CPC ..................... A61B 17/0401; A61B 17/06166; A61B 2017/0406; A61B 2017/06176; A61B 2017/00867; A61B 2017/00871; A61B 2017/0404; A61B 2017/041
USPC .......................................... 606/151, 224–232
See application file for complete search history.

(56) References Cited

U.S. PATENT DOCUMENTS 3,657,056 A 4/1972 Winston et al.
3,985,138 A * 10/1976 Jarvik ........................... 606/231
(Continued)

FOREIGN PATENT DOCUMENTS

EP 0494636 A 7/1992
EP 0499048 A1 8/1992
(Continued)

OTHER PUBLICATIONS

European Search Report for EP 11250537.1269 date of completion is Aug. 8, 2011 (3 pages).
(Continued)

*Primary Examiner* — Julian W Woo

(57) ABSTRACT

A medical device includes an elongate body having a proximal portion and a distal portion. The proximal portion of the elongate body terminates in a free end and the distal portion forms a loop. The loop includes a proximal portion and a distal portion, and a plurality of barbs disposed along a surface thereof. A pledget is disposed adjacent the proximal portion of the loop. The elongate body, loop, and/or barbs may be formed from shape memory polymers that are configured to change shape in vivo upon application of energy. Methods for securing medical devices of the present disclosure are also disclosed.

31 Claims, 10 Drawing Sheets

(52) U.S. Cl.
CPC .................. *A61B2017/0412* (2013.01); *A61B 2017/06176* (2013.01)

(56) References Cited

U.S. PATENT DOCUMENTS

| | | | |
|---|---|---|---|
| 4,024,871 A | 5/1977 | Stephenson | |
| 4,950,285 A * | 8/1990 | Wilk | 606/232 |
| 5,019,093 A | 5/1991 | Kaplan et al. | |
| 5,059,213 A | 10/1991 | Chesterfield et al. | |
| 5,123,913 A | 6/1992 | Wilk et al. | |
| 5,133,738 A | 7/1992 | Korthoff et al. | |
| 5,181,923 A | 1/1993 | Chesterfield et al. | |
| 5,219,359 A * | 6/1993 | McQuilkin et al. | 606/232 |
| 5,226,912 A | 7/1993 | Kaplan et al. | |
| 5,236,563 A | 8/1993 | Loh | |
| 5,261,886 A | 11/1993 | Chesterfield et al. | |
| 5,306,289 A | 4/1994 | Kaplan et al. | |
| 5,318,575 A | 6/1994 | Chesterfield et al. | |
| 5,342,376 A | 8/1994 | Ruff | |
| 5,370,031 A | 12/1994 | Koyfman et al. | |
| 5,383,387 A | 1/1995 | Chesterfield et al. | |
| 5,383,883 A | 1/1995 | Wilk et al. | |
| 5,417,700 A | 5/1995 | Egan | |
| 5,507,777 A * | 4/1996 | Kus et al. | 606/224 |
| 5,569,302 A | 10/1996 | Proto et al. | |
| 5,662,682 A | 9/1997 | Chesterfield et al. | |
| 5,667,528 A | 9/1997 | Colligan | |
| 5,814,056 A | 9/1998 | Prosst et al. | |
| 5,830,234 A | 11/1998 | Wojciechowicz et al. | |
| 5,893,880 A | 4/1999 | Egan et al. | |
| 5,931,855 A | 8/1999 | Buncke | |
| 5,964,765 A | 10/1999 | Fenton, Jr. et al. | |
| 5,968,077 A | 10/1999 | Wojciechowicz et al. | |
| 6,063,105 A | 5/2000 | Totakura | |
| 6,106,505 A | 8/2000 | Modak et al. | |
| 6,143,352 A | 11/2000 | Clark et al. | |
| 6,165,202 A | 12/2000 | Kokish et al. | |
| 6,174,324 B1 | 1/2001 | Egan et al. | |
| 6,203,564 B1 | 3/2001 | Hutton et al. | |
| 6,217,591 B1 | 4/2001 | Egan et al. | |
| 6,235,869 B1 | 5/2001 | Roby et al. | |
| 6,241,747 B1 | 6/2001 | Ruff | |
| 6,286,746 B1 | 9/2001 | Egan et al. | |
| 6,293,961 B2 * | 9/2001 | Schwartz et al. | 606/232 |
| 6,488,690 B1 | 12/2002 | Morris et al. | |
| 6,506,197 B1 | 1/2003 | Rollero et al. | |
| 6,562,051 B1 | 5/2003 | Bolduc et al. | |
| 6,599,310 B2 | 7/2003 | Leung et al. | |
| 6,620,846 B1 | 9/2003 | Jonn et al. | |
| 6,692,499 B2 | 2/2004 | Tormala et al. | |
| 6,773,450 B2 | 8/2004 | Leung et al. | |
| 6,923,824 B2 | 8/2005 | Morgan et al. | |
| 7,021,316 B2 * | 4/2006 | Leiboff | 606/151 |
| 7,090,111 B2 | 8/2006 | Egan et al. | |
| 8,100,941 B2 * | 1/2012 | Lindh et al. | 606/228 |
| 2002/0077661 A1 | 6/2002 | Saadat | |
| 2002/0177876 A1 | 11/2002 | Roby et al. | |
| 2003/0074023 A1 | 4/2003 | Kaplan et al. | |
| 2003/0097148 A1 | 5/2003 | Valimaa et al. | |
| 2003/0149447 A1 | 8/2003 | Morency et al. | |
| 2004/0010275 A1 | 1/2004 | Jacobs et al. | |
| 2004/0030354 A1 | 2/2004 | Leung et al. | |
| 2004/0060409 A1 | 4/2004 | Leung et al. | |
| 2004/0060410 A1 | 4/2004 | Leung et al. | |
| 2004/0087974 A1 | 5/2004 | Bitter | |
| 2004/0088003 A1 * | 5/2004 | Leung et al. | 606/228 |
| 2004/0122451 A1 | 6/2004 | Wood | |
| 2004/0153125 A1 | 8/2004 | Roby | |
| 2004/0162580 A1 | 8/2004 | Hain | |
| 2005/0033367 A1 | 2/2005 | Leung et al. | |
| 2005/0049635 A1 | 3/2005 | Leiboff | |
| 2005/0165448 A1 | 7/2005 | Egan et al. | |
| 2005/0209639 A1 | 9/2005 | Gidwani et al. | |
| 2005/0216058 A1 | 9/2005 | Egan et al. | |
| 2005/0267479 A1 | 12/2005 | Morgan et al. | |
| 2005/0267531 A1 * | 12/2005 | Ruff et al. | 606/228 |
| 2006/0116718 A1 | 6/2006 | Leiboff | |
| 2006/0206096 A1 | 9/2006 | Accisano, III et al. | |
| 2007/0005110 A1 | 1/2007 | Collier et al. | |
| 2007/0021780 A1 | 1/2007 | Harrington et al. | |
| 2007/0083236 A1 * | 4/2007 | Sikora et al. | 606/232 |
| 2007/0187861 A1 | 8/2007 | Genova | |
| 2007/0224237 A1 | 9/2007 | Hwang et al. | |
| 2008/0281357 A1 * | 11/2008 | Sung et al. | 606/232 |
| 2009/0125038 A1 * | 5/2009 | Ewers et al. | 606/142 |
| 2009/0306681 A1 * | 12/2009 | Del Nido et al. | 606/139 |

FOREIGN PATENT DOCUMENTS

| | | |
|---|---|---|
| EP | 0 632 999 A1 | 1/1995 |
| EP | 0632999 A | 1/1995 |
| EP | 0647452 A1 | 4/1995 |
| EP | 1669093 | 6/2006 |
| EP | 1656890 B1 | 12/2008 |
| EP | 2 106 752 A1 | 10/2009 |
| WO | WO 91/07916 A1 | 6/1991 |
| WO | WO 97/08238 | 3/1997 |
| WO | WO 98/00065 | 1/1998 |
| WO | WO 98/52473 | 11/1998 |
| WO | WO 99/52451 A | 10/1999 |
| WO | WO00/57933 A1 | 10/2000 |
| WO | WO 01/52751 A | 7/2001 |
| WO | WO03/001979 A2 | 1/2003 |
| WO | WO2004/014236 A1 | 2/2004 |
| WO | WO2004/030520 A2 | 4/2004 |
| WO | WO2004/030704 A2 | 4/2004 |
| WO | WO2004/030705 A2 | 4/2004 |
| WO | WO2004/045663 A2 | 6/2004 |
| WO | WO2004/066927 A2 | 8/2004 |
| WO | WO2005/080495 | 1/2005 |
| WO | WO2006/079469 | 8/2006 |
| WO | WO 2007/133103 A | 11/2007 |
| WO | WO 2007/133103 A1 | 11/2007 |
| WO | WO 2008/042909 A | 4/2008 |
| WO | WO 2008/107919 A | 9/2008 |
| WO | WO 2008/141034 A1 | 11/2008 |

OTHER PUBLICATIONS

European Search Report for EP 10177651.6-1526 date of completion is Dec. 14, 2010 (3 pages).
U.S. Appl. No. 60/994,173, filed Sep. 17, 2007, Maiorino et al.
European Search Report for EP 092510346-1265 date of completion is May 26, 2009 (3 pages).
European Search Report for Application No. 09250460 date Jun. 2, 2009.
European Search Report for Application No. 09251035.3 date Jun. 3, 2009.
European Search Report from Application No. 07254341 dated Apr. 20, 2009.
European Search Report from Application No. 07254703 dated Feb. 10, 2009.
JLT1204-211-229(175):R.R. Szarmach et al., Journal of Long-Term Effects of Medical Implants, "An Innovative Surgical Suture and Needle . . . " 12(4), pp. 211-229(2002).
George Odian, "Principles of Polymerization," III Edition, pp. 569-573(1991).
International Search Report from Appln. No. EP 06 012688 dated Aug. 1, 2007.
European Search Report from Appln. No. EP 07 253438 dated Feb. 1, 2008.
European Search Report for EP 12169125.7-1269 date of completion is Jun. 22, 2012 (5 pages).
European Search Report for EP 12166183.9-1269 date of completion is Jul. 5, 2012 (8 pages).

* cited by examiner

ND DEVICE

CROSS-REFERENCE TO RELATED APPLICATIONS

This application is a continuation in part of U.S. patent application Ser. No. 12/416,421 filed Apr. 1, 2009, which is a continuation in part of U.S. patent application Ser. No. 12/362,002 filed Jan. 29, 2009, which claims the benefit of and priority to U.S. Provisional Patent Application 61/041,302 filed Apr. 1, 2008, the disclosure of which is hereby incorporated by reference herein.

TECHNICAL FIELD

The present disclosure relates generally to the field of surgical devices, and more particularly to anchoring devices, such as sutures, which include a loop having barbs disposed along a surface.

BACKGROUND OF RELATED ART

Surgical sutures have been successfully used for various types of medical procedures, including tissue and wound closure. Surgical sutures typically have a needle attached at one end. As the needle penetrates tissue, the suture enters, passes through, and exits tissue, at which point knots may be used to secure the tissue or wound.

Additionally, sutures typically employ a knot at the distal end to secure the suture end in tissue, permitting movement of the free end through tissue. Knot tying adds time to a procedure and may result in additional bulk material being left at the wound site. Improvements in the field are desired.

Furthermore, specific patient populations such as patients with diabetes T1, T2, or other immuno-compromised patients (such as chemotherapy patients) have less elastic tissue. These patient populations have longer healing profiles and less compliant tissue and these factors may lead to lower suture holding forces in tissue. Needles tend to be oversized for given suture diameter and a larger needle may leave behind a larger hole at the needle penetration point in the tissue. The suture generally needs to fill this hole. Also, improvements in suture holding forces are desired.

SUMMARY

The present disclosure provides medical devices, as well as methods for making and using same. In embodiments, a medical device of the present disclosure may include an elongate body having a proximal portion and a distal portion, the proximal portion of the elongate body terminating in a free end; the distal portion of the elongate body forming a loop including a first plurality of barbs disposed along the surface of the loop; and, a pledget disposed adjacent the proximal portion of the loop, wherein at least one of the elongate body, the loop, and the barbs comprises a shape memory polymer.

Methods of the present disclosure may include, in embodiments, providing a medical device including an elongate body having a proximal portion and a distal portion, the proximal portion of the elongate body terminating in a free end, the distal portion of the elongate body forming a loop, the loop including a first plurality of barbs disposed along a surface of the loop, and a pledget disposed adjacent the proximal portion of the loop, wherein at least one of the elongate body, the loop, and the barbs, comprises a shape memory polymer; inserting a proximal portion of the medical device into tissue; pulling the elongate body through tissue; advancing the proximal portion of the elongate body through tissue; and, applying energy to the elongate body, the loop, or the barbs, such that at least one of the elongate body, the loop, and the barbs limits movement of the proximal portion of the loop through the tissue.

BRIEF DESCRIPTION OF DRAWINGS

Various preferred embodiments of the sutures are described herein with reference to the drawings, in which.

DETAILED DESCRIPTION OF EMBODIMENTS

Figure 1A:
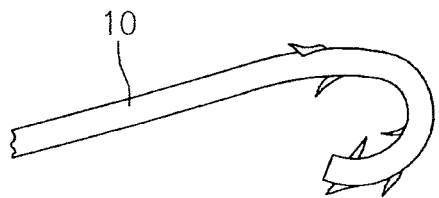
FIGS. 1A-1B are side views illustrating one embodiment of a looped suture.

The present disclosure is directed to an anchoring device and in certain preferred embodiments, a suture, herein referred to as an anchoring suture. The anchoring sutures of certain embodiments of the present disclosure have an elongate body, which connects to a needle at a proximal end thereof, and a distal end of the elongate body forms an anchoring loop. The anchoring loop further includes a plurality of barbs (tissue engaging barbs). Medical devices of the present disclosure include sutures formed from fibers, filaments, and yarns.

Anchoring devices, including anchoring sutures and pledgets of the present disclosure may be absorbable or non-absorbable. It should be understood that combinations of filaments made from different materials (e.g., natural and synthetic, or bioabsorbable and non-bioabsorbable materials) may be used to make the present anchoring suture.

Suitable synthetic absorbable materials include polymers such as those made from lactide, glycolide, caprolactone, valerolactone, carbonates (e.g., trimethylene carbonate, tetramethylene carbonate), dioxanones (e.g., 1,4-dioxanone), 1-dioxepanones (e.g., 1,4-dioxepan-2-one and 1,5-dioxepan-2-one), ethylene glycol, ethylene oxide, esteramides, γ-hydroxyvalerate, β-hydroxypropionate, alpha-hydroxy acid, hydroxybuterates, orthoesters, hydroxy alkanoates, tyrosine carbonates, polyimide carbonates, polyimino carbonates such as poly(bisphenol A-iminocarbonate) and poly(hydroquinone-iminocarbonate), and polymer drugs (e.g., polydiflunisol, polyaspirin, and protein therapeutics), and the like, and copolymers and combinations thereof. Suitable natural absorbable polymers include collagen, cellulose, gut, combinations thereof and the like. In embodiments, glycolide and lactide based polyesters, including copolymers of lactide and glycolide may be used.

Suitable non-absorbable materials which may be used to form the anchoring sutures disclosed herein include non-absorbable natural materials such as cotton, silk, and rubber. Suitable non-absorbable synthetic materials include monomers and polymers derived from materials such as nylons, polyolefins such as polypropylene and polyethylene, (including ultra high molecular weight polyethylene (UHMWPE)), polyamides, polyesters such as poly ethylene terephthalate (PET), polyaryletherketone, polyvinylidene difluoride (PVDF), acrylic, polyamides, aramids, fluropolymers, polybutesters, silicones, and polymer blends, copolymers thereof, combinations with degradable polymers, and the like. Polypropylene can also be utilized to form the suture. The polypropylene can be isotactic polypropylene or a mixture of isotactic and syndiotactic or atactic polypropylene, combinations thereof, and the like. Additionally, non-absorbable synthetic and natural polymers and monomers may be combined with each other and may also be combined with various absorbable polymers and monomers to create fibers and filaments for the present anchored device.

In embodiments, suitable materials which may be utilized to form the anchoring devices in accordance with the present disclosure include homopolymers, copolymers, and/or blends possessing glycolic acid, lactic acid, glycolide, lactide, dioxanone, trimethylene carbonate, caprolactone, and various combinations of the foregoing. For example, in some embodiments, a copolymer of glycolide and trimethylene carbonate may be utilized. Methods for forming such copolymers are within the purview of those skilled in the art and include, for example, the methods disclosed in U.S. Pat. Nos. 4,300,565 and 5,324,307, the entire disclosures of each or which are incorporated by reference herein. Suitable copolymers of glycolide and trimethylene carbonate may possess glycolide in amounts from about 60% to about 75% by weight of the copolymer, in embodiments, from about 65% to about 70% by weight of the copolymer, with the trimethylene carbonate being present in amounts from about 25% to about 40% by weight of the copolymer, in embodiments, from about 30% to about 35% by weight of the copolymer.

Other suitable materials include copolymers of lactide and glycolide, with lactide present in an amount from about 6% to about 12% by weight of the copolymer and glycolide being present in amounts from about 88% to about 94% by weight of the copolymer. In some embodiments, lactide is present from about 7% to about 11% by weight of the copolymer with glycolide being present in amounts from about 89% to about 98% by weight of the copolymer. In some other embodiments, lactide is present in an amount of about 9% by weight of the copolymer with the glycolide being present in an amount of about 91% by weight of the copolymer.

In embodiments, suitable materials for forming anchoring devices according to the present disclosure include copolymers of glycolide, dioxanone, and trimethylene carbonate. Such materials may include, for example, copolymers possessing glycolide in amounts from about 55% to about 65% by weight of the copolymer, in embodiments, from about 58% to about 62% by weight of the copolymer, in some embodiments, about 60% by weight of the copolymer; dioxanone in amounts from about 10% to about 18% by weight of the copolymer, in embodiments, from about 12% to about 16% by weight of the copolymer, in some embodiments about 14% by weight of the copolymer; and trimethylene carbonate in amounts from about 17% to about 35% by weight of the copolymer, in embodiments, from about 22% to about 30% by weight of the copolymer, in some embodiments, about 26% by weight of the copolymer.

Other suitable materials including a copolymer of glycolide, lactide, trimethylene carbonate, and ε-caprolactone may be utilized to form anchoring devices in accordance with the present disclosure. Such materials may include, for example, a random copolymer possessing caprolactone in amounts from about 14% to about 20% by weight of the copolymer, in embodiments, from about 16% to about 18% by weight of the copolymer, in some embodiments, about 17% by weight of the copolymer; lactide in amounts from about 4% to about 10% by weight of the copolymer, in embodiments, from about 6% to about 8% by weight of the copolymer, in some embodiments about 7% by weight of the copolymer; trimethylene carbonate in amounts from about 4% to about 10% by weight of the copolymer, in embodiments from about 6% to about 8% by weight of the copolymer, in some embodiments about 7% by weight of the copolymer; and glycolide in amounts from about 60% to about 78% by weight of the copolymer, in embodiments, from about 66% to about 72% by weight of the copolymer, in some embodiments about 69% by weight of the copolymer.

In certain embodiments, anchoring devices, including anchoring sutures and pledgets, may, in whole or in part (e.g. barbs) may be constructed using shape memory polymers. The present disclosure provides anchoring devices, including anchoring sutures and pledgets, formed of shape memory polymeric materials which are capable of adopting a shape in vivo suitable for adhering tissue or affixing a surgical device, such as a mesh, to tissue. Shape memory polymeric materials utilized to form an anchoring device of the present disclosure possess a permanent shape and a temporary shape. In embodiments, the temporary shape is of a configuration which enhances the ability for the surgeon to introduce an anchoring device into a patient's body. The permanent shape, which is assumed in vivo upon application of energy, such as heat or light, is of a configuration which enhances the retention of the anchoring device in tissue and/or adhesion of the anchoring device to tissue.

Shape memory polymers are a class of polymers that, when formed into an object such as an anchoring device, can be temporarily deformed by mechanical force and then caused to revert back to an original shape when stimulated by energy. Shape memory polymers exhibit shape memory properties by virtue of at least two phase separated microdomains in their microstructure. The first domain is composed of hard, covalently cross-linked or otherwise chain motion-limiting structures, which act as barbs to retain the object's original shape. The second domain is a switchable soft structure, which can be deformed and then fixed to obtain a secondary or temporary shape.

In the case of heat stimulated shape memory polymers, a transition temperature ($T_{Trans}$) exists at which the shape change occurs during heating. The shape memory polymers can thus be tailored by altering material properties at the molecular level and by varying processing parameters. An object's primary shape may be formed with heat and pressure at a temperature at which the soft domains are flexible and the hard domains are not fully formed. The object may then be cooled so that the hard domains are more fully formed and the soft domains become rigid. The secondary or temporary shape can be formed by mechanically deforming the object, which is most readily accomplished at a temperature approaching or above $T_{Trans}$. Mechanical stresses introduced into the object are then locked into place by cooling the object to temperatures below $T_{Trans}$, so that the soft segments solidify to a rigid state. Once the object is heated to $T>T_{Trans}$, the soft segments soften and relax back to their original configuration and the object returns to its primary or original shape, sometimes referred to herein as its permanent shape. The temperature at which a shape memory material reverts to its permanent shape may be referred to, in embodiments, as its permanent temperature ($T_{perm}$).

Polymers possessing shape memory properties which may be used to construct anchoring devices disclosed herein include, for example, synthetic materials, natural materials (e.g., biological) and combinations thereof, which may be biodegradable and/or non-biodegradable. As used herein, the term "biodegradable" includes both bioabsorbable and bioresorbable materials. By biodegradable, it is meant that the materials decompose or lose structural integrity under body conditions (e.g., enzymatic degradation, hydrolysis), or are broken down (physically or chemically) under physiologic conditions in the body (e.g., dissolution) such that the degradation products are excretable or absorbable by the body.

Suitable non-degradable materials possessing shape memory properties which may be utilized to form an anchoring device include, but are not limited to, polyolefins such as polyethylene (including ultra high molecular weight polyethylene) and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins such as fluoroethylenes, fluoropropylenes, fluoroPEGs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polytetramethylene ether glycol; polybutesters, including copolymers of butylene terephthalate and polytetramethylene ether glycol; 1,4-butanediol; polyurethanes; acrylic polymers; methacrylics; vinyl halide polymers and copolymers such as polyvinyl chloride; polyvinyl alcohols; polyvinyl ethers such as polyvinyl methyl ether; polyvinylidene halides such as polyvinylidene fluoride and polyvinylidene chloride; polychiorofluoroethylene; polyacrylonitrile; polyaryletherketones; polyvinyl ketones; polyvinyl aromatics such as polystyrene; polyvinyl esters such as polyvinyl acetate; copolymers of vinyl monomers with each other and olefins such as ethylene-methyl methacrylate copolymers; acrylonitrile-styrene copolymers; acrylonitrile, butadiene and styrene (ABS) resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof. Additionally, non-biodegradable polymers and monomers may be combined with each other.

Suitable bioabsorbable polymers possessing shape memory properties which may be utilized to form an anchoring device include, but are not limited to, aliphatic polyesters; polyamides; polyamines; polyalkylene oxalates; poly(anhydrides); polyamidoesters; copoly(ether-esters); poly(carbonates) including tyrosine derived carbonates; poly(hydroxyalkanoates) such as poly(hydroxybutyric acid), poly(hydroxyvaleric acid), and poly(hydroxybutyrate); polyimide carbonates; poly(imino carbonates) such as poly(bisphenol A-iminocarbonate and the like); polyorthoesters; polyoxaesters including those containing amine groups; polyphosphazenes; poly(propylene fumarates); polyurethanes; polymer drugs such as polydiflunisol, polyaspirin, and protein therapeutics; biologically modified (e.g., protein, peptide) bioabsorbable polymers; and copolymers, block copolymers, homopolymers, blends, and combinations thereof.

Suitable aliphatic polyesters which may be utilized to form an anchoring device include, but are not limited to, homopolymers and copolymers of lactide (including lactic acid, D-, L- and meso lactide); glycolide (including glycolic acid); epsilon-caprolactone; p-dioxanone (1,4-dioxan-2-one); trimethylene carbonate (1,3-dioxan-2-one); alkyl derivatives of trimethylene carbonate; Δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α,α diethylpropiolactone; ethylene carbonate; ethylene oxalate; 3-methyl-1,4-dioxane-2,5-dione; 3,3-diethyl-1,4-dioxan-2,5-dione; 6,8-dioxabicycloctane-7-one; and polymer blends and copolymers thereof.

Other suitable biodegradable polymers which may be utilized to form an anchoring device include, but are not limited to, poly(amino acids) including proteins such as collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, and cellulose; glycosaminoglycan; gut; and combinations thereof. Collagen as used herein includes natural collagen such as animal derived collagen, gelatinized collagen, or synthetic collagen such as human or bacterial recombinant collagen.

Additionally, synthetically modified natural polymers such as cellulose and polysaccharide derivatives, including alkyl celluloses, hydroxyalkyl celluloses, cellulose ethers, cellulose esters, nitrocelluloses, and chitosan may be utilized. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose (CMC), cellulose triacetate, and cellulose sulfate sodium salt. These may be collectively referred to herein, in embodiments, as "celluloses."

In embodiments, combinations of both degradable and non-degradable materials, including those having shape memory characteristics, may be utilized to form an anchoring device.

In embodiments, the shape memory polymer may be a copolymer of two components with different thermal characteristics, such as oligo (epsilon-caprolactone) dimethacrylates and butyl acrylates, including poly(epsilon-caprolactone) dimethacrylate-poly(n-butyl acrylate), or a diol ester and an ether-ester diol such as oligo (epsilon caprolactone) diol/oligo (p-dioxanone) diol copolymers. These multi-block oligo (epsilon-caprolactone) diol/oligo (p-dioxanone) diol copolymers possess two block segments: a "hard" segment and a "switching" segment linked together in linear chains. Such materials are disclosed, for example, in Lendlein, "Shape Memory Polymers-Biodegradable Sutures," Materials World, Vol. 10, no. 7, pp. 29-30 (July 2002), the entire disclosure of which is incorporated by reference herein.

In other embodiments, blends of bioabsorbable materials may be utilized to form anchoring devices including, but not limited to, urethanes blended with lactic acid and/or glycolic acid, homopolymers thereof or copolymers thereof, and acrylates blended with caprolactones such as polycaprolactone dimethacrylate poly(butyl acrylate) blends, and combinations thereof.

Other examples of suitable shape memory polymers and means for forming permanent and temporary shapes therewith are set forth in Lendlein et al., "Shape memory polymers as stimuli-sensitive implant materials," Clinical Hemorheology and Microcirculation, 32 (2005) 105-116, Lendlein et al., "Biodegradable, Elastic Shape memory Polymers for Potential Biomedical Applications," Science, Vol. 269 (2002) 1673-1676, and Lendlein et al., "Shape-Memory Polymers," Angew. Chem. Int. Ed., 41 (2002) 2035-2057, the entire disclosures of each of which are incorporated by reference herein.

Table 1 below further illustrates compositions which demonstrate shape memory effects. The block copolymers of each composition are in annealed wire format, the proposed soft and hard segments, and the glass transition temperature ($T_g$), having been measured by differential scanning calorimetry which is equal to $T_{Trans}$.

TABLE 1

| Composition (mol %) | Soft Domain | Hard Domain | $T_g$ ($T_{Trans}$) [° C.] |
|---|---|---|---|
| 15% Polydioxanone 85% Poly (L-lactide) | Polydioxanone and Amorphous Polylactide | Crystalline Polylactide | 54 |
| 20% Polydioxanone 80% Poly (L-lactide) | Polydioxanone and Amorphous Polylactide | Crystalline Polylactide | 45 |
| 15% Trimethylene Carbonate 85% Poly (L-lactide) | Trimethylene Carbonate and Amorphous Polylactide | Crystalline Polylactide | 54 |
| 20% Trimethylene Carbonate 80% Poly (L-lactide) | Trimethylene Carbonate and Amorphous Polylactide | Crystalline Polylactide | 55 |

The copolymers in Table 1 may undergo a partial shift when approaching $T_g$, and $T_{Trans}$ may be depressed when the materials are in aqueous solution. Since these polymers degrade by water absorption and bulk hydrolysis, water molecules entering the polymer matrices may act as plasticizers, causing the soft segments to soften at lower temperatures than in dry air. Thus, polymers exhibiting $T_{Trans}$ depression in aqueous solution may maintain a temporary shape through temperature excursions in the dry state, such as during shipping and storage, and shape shift to its permanent shape at body temperatures upon implantation.

Thus, in embodiments, the shape memory polymer may include a block copolymer of polydioxanone and polylactide with the polydioxanone present in an amount from about 5 mol % to about 20 mol % of the copolymer, in embodiments from about 15 mol % to about 19 mol % of the copolymer, and the polylactide present in an amount from about 80 mol % to about 95 mol % of the copolymer, in embodiments from about 81 mol % to about 85 mol % of the copolymer. In other embodiments, the shape memory polymer may include a block copolymer of trimethylene carbonate and polylactide, with the trimethylene carbonate present in an amount from about 5 mol % to about 20 mol % of the copolymer, in embodiments from about 15 mol % to about 19 mol % of the copolymer, and the polylactide may be present in an amount from about 80 mol % to about 95 mol % of the copolymer, in embodiments from about 81 mol % to about 85 mol % of the copolymer.

It is envisioned that $T_{Trans}$ may be tailored by changing block segment molar ratios, polymer molecular weight, and time allowed for hard segment formation. In embodiments, $T_{Trans}$ may be tailored by blending various amounts of low molecular weight, oligomers of the soft segment domain copolymer. Such oligomers may act as plasticizers to cause a downward shift in $T_{Trans}$.

Additionally, the copolymers forming the anchoring devices of the present disclosure may include emulsifying agents, solubilizing agents, wetting agents, taste modifying agents, plasticizers, active agents, water soluble inert fillers, preservatives, buffering agents, coloring agents, and stabilizers. Addition of a plasticizer to the formulation can improve flexibility. The plasticizer or mixture of plasticizers may be polyethylene glycol, glycerol, sorbitol, sucrose, corn syrup, fructose, dioctyl-sodium sulfosuccinate, triethyl citrate, tributyl citrate, 1,2-propylenglycol, mono-, di- or triacetates of glycerol, or natural gums.

In some embodiments, crystalline degradable salts or minerals may be added to the block copolymer compositions to create polymer composites which may improve shape memory properties. An example of such a composite using polylactide homopolymer and crystalline hydroxyapatite is described in Zheng et al., "Shape memory properties of poly (D,L-lactide/hydroxyapatite composites," Biomaterials, 27 (2006) 4288-4295, the entire disclosure of which are incorporated by reference herein.

Other shape memory materials, including shape memory metals and metal alloys such as Nitinol, may also be used to form the anchoring devices, including anchoring sutures and pledgets, of the present disclosure.

In embodiments, a molding process may be utilized to produce the anchoring devices of the present disclosure. Plastic molding methods are within the purview of those skilled in the art and include, but are not limited to, melt molding, solution molding, and the like. Injection molding, extrusion molding, compression molding and other methods can also be used as the melt molding technique. Once placed in the mold with the proper dimensions and configuration, the polymeric material used to form the anchoring device may be heated to a suitable temperature, referred to as the permanent temperature ($T_{perm}$) which may, in embodiments, be the melting temperature of the shape memory polymeric material utilized to form the anchoring device. Heating of the anchoring device may be at suitable temperatures including, for example, from about 40° C. to about 180° C., in embodiments from about 80°

C. to about 150° C., for a period of time of from about 2 minutes to about 60 minutes, in embodiments from about 15 minutes to about 20 minutes, to obtain the permanent shape and dimensions.

The temperature for deformation treatment of the anchoring member molded with a previously memorized shape is one that makes possible ready deformation without producing cracks and should not exceed the temperature adopted for the shape memorization (e.g.; $T_{perm}$). Deformation treatment at a temperature exceeding that for the original shape memorization may cause the object to memorize/program a new deformed shape.

After the anchoring device with the desired shape has been formed, the anchoring device may be deformed above $T_{trans}$ obtain an alternate, temporary shape.

Suitable temperatures for deformation will vary depending on the shape memory polymer utilized, but generally may be above the transition temperature of the polymer ($T_{trans}$), but below the $T_{perm}$. In embodiments, the shape memory polymer may be cooled from its $T_{perm}$ to a lower temperature which remains above the $T_{trans}$ and deformed, in embodiments by hand and/or mechanical means. In other embodiments, the anchoring device may be deformed at room temperature (about 20° C. to about 25° C.) to obtain its temporary shape, although the temperature may differ depending upon the particular polymer employed. The anchoring device may then be cooled to a temperature below the $T_{trans}$ of the material utilized to form the anchoring device at which time the anchoring device of the present disclosure is ready for use. As the $T_{trans}$ is usually greater than room temperature, in embodiments cooling to room temperature may be sufficient to lock in the temporary shape.

There are no particular limitations on the manner in which the deformation can be achieved. Deformation can be achieved either by hand or by means of a suitable device selected to provide the desired temporary configuration to the anchoring device.

In order to keep the shape of the anchoring device in its temporary shape, the shape memory anchoring device of the present disclosure should be stored at a temperature which will not cause a transition to the primary shape. In embodiments, the shape memory anchoring device may be stored in a refrigerator.

In embodiments, the shape memory polymeric materials of the present disclosure may be compressed or expanded into temporary forms that are smaller or larger in diameter than their permanent shape.

The anchoring devices thus prepared recover their primary shape upon application of energy, such as on heating, either by placement in a patient's body, or the addition of exogenous heat at a prescribed temperature, in embodiments above the $T_{trans}$ of the shape memory polymer utilized. As the anchoring devices of the present disclosure are utilized in a living body, heating with body heat (about 37° C.) is possible. In such a case, the temperature for shape programming should be as low as possible and the recovery of the primary (memorized) shape may occur fairly slowly. In embodiments, recovery of the permanent shape may occur from about 1 second to about 5 seconds after insertion into tissue.

However, in some embodiments a higher shape memory temperature may be desirable in order to make the shape recover at a slightly higher temperature than body temperature. Thus, in some cases, releasing the anchoring device from deformation to recover the primary shape can be achieved by heating. On heating at a temperature of from about 30° C. to about 50° C., in embodiments from about 37° C. to about 43° C., the temporary shape may be released and the primary shape recovered. The higher the temperature for heating, the shorter the time for recovery of the primary shape. The means for this heating is not limited. Heating can be accomplished by using a gas or liquid heating medium, heating devices, ultrasonic waves, electrical induction, and the like. Examples of liquid heating media include physiological saline solution, alcohol, combinations thereof, and the like. Of course, in an application involving a living body, care may be taken to utilize a heating temperature which will not cause burns. When a liquid heating medium is used, physiological saline solution or alcohol may be desirable.

Similarly, in other embodiments, electrically active polymers, also known as electroactive polymers, which can alter their configuration upon application of electricity, may be utilized to fashion anchoring devices, including anchoring sutures and pledgets, in accordance with the present disclosure. Suitable examples of electroactive polymers include poly(aniline), substituted poly(aniline)s, polycarbazoles, substituted polycarbazoles, polyindoles, poly(pyrrole)s, substituted poly(pyrrole)s, poly(thiophene)s, substituted poly(thiophene)s, poly(acetylene)s, poly(ethylene dioxythiophene)s, poly(ethylenedioxypyrrole)s, poly(p-phenylene vinylene)s, and the like, or combinations including at least one of the foregoing electroactive polymers. Blends or copolymers or composites of the foregoing electroactive polymers may also be used.

Similar to the change in shape which a shape memory material may undergo upon the application of energy, such as heat, in embodiments an electroactive polymer may undergo a change in shape upon the application of electricity from a low voltage electrical source (such as a battery). Suitable amounts of electricity which may be applied to effect such change will vary with the electroactive polymer utilized, but can be from about 5 volts to about 30 volts, in embodiments from about 10 volts to about 20 volts. The application of electricity will result in the anchoring device constructed of the electroactive polymer changing its shape into an anchoring configuration.

While an electroactive polymer does not have the same permanent shape and temporary shape as those terms are described above with respect to shape memory polymers, as used herein the term "permanent shape" as applied to an electroactive polymer means, in embodiments, the shape the electroactive polymer adopts upon the application of electricity, and the term "temporary shape" as applied to an electroactive polymer means, in embodiments, the shape of the electroactive polymer adopts in the absence of electricity.

In some embodiments, the sutures may include metals (e.g. steel and degradable magnesium), metal alloys or the like.

In embodiments, the anchoring suture and the pledget may be made of materials having the same or similar degradation rates, i.e., they will each degrade in about the same period of time, in embodiments from about 0 days to about 180 days after placement in a patient. More specifically the anchoring suture and pledget may both include homopolymers, copolymers, and/or blends possessing glycolic acid, lactic acid, glycolide, lactide, dioxanone, trimethylene carbonate, caprolactone, and various combinations of the foregoing. For example, in some embodiments, a copolymer of glycolide and trimethylene carbonate may be utilized. Suitable copolymers of glycolide and trimethylene carbonate may possess glycolide in amounts from about 60% to about 75% by weight of the copolymer, in embodiments, from about 65% to about 70% by weight of the copolymer, with the trimethylene carbonate being present in amounts from about 25% to about 40% by weight of the copolymer, in embodiments, from about 30% to about 35% by weight of the copolymer. In embodiments, anchoring sutures and/or pledgets made of these copolymers may provide effective wound support for about 6 weeks, and absorbing in about 180 days.

In another embodiment, the anchoring suture and pledget may both include copolymers of glycolide, dioxanone, and trimethylene carbonate. Such materials may include, for example, copolymers possessing glycolide in amounts from about 55% to about 65% by weight of the copolymer, in embodiments, from about 58% to about 62% by weight of the copolymer, in some embodiments, about 60% by weight of the copolymer; dioxanone in amounts from about 10% to about 18% by weight of the copolymer, in embodiments, from about 12% to about 16% by weight of the copolymer, in some embodiments about 14% by weight of the copolymer; and trimethylene carbonate in amounts from about 17% to about 35% by weight of the copolymer, in embodiments, from about 22% to about 30% by weight of the copolymer, in some embodiments, about 26% by weight of the copolymer. In embodiments, anchoring sutures and/or pledgets made of these copolymers may provide effective wound support for about 3 weeks, and absorbing, sometimes referred to herein as "losing structural integrity," from about 90 days to about 110 days after placement in a patient.

The anchoring suture and pledget should have about the same or similar wound support. Thus, in other embodiments, the anchoring suture and pledget may include different materials or have different degradation times, as long as the wound support provided by each component is similar.

In embodiments, two or more of the elongate body, pledget and barbs may lose strength and/or structural integrity in about the same period of time, in embodiments from about 1 day to about 6 weeks.

As used herein, the terms "fibers", "filaments" and "yarns" each may be used to construct in whole or in part anchoring devices. The term "fibers," in this context, are generally used to designate natural or synthetic structures that have a length approximately 3 orders of magnitude greater than their diameter or width. The term "filaments" are typically used to describe "fibers" of indefinite or extreme length, and "yarns" as a generic term for a continuous strand of twisted or untwisted "fibers" or "filaments" in a form suitable for knitting, weaving, braiding or otherwise intertwining.

In embodiments, sutures of the present disclosure may possess a core/sheath configuration. Fibers may possess a core/sheath configuration, yarns may possess a core/sheath configuration, or both. Any material described herein, including the shape memory materials described above, may be utilized to form the core, the sheath, or both.

Sutures of the present disclosure may be monofilament or multifilament (e.g. braided). Methods for making sutures from these suitable materials are within the purview of those skilled in the art (e.g. extrusion and molding). The filaments may be combined to create a multifilament suture using any technique within the purview of one skilled in the art such as commingling, twisting, braiding, weaving, entangling, and knitting. For example, filaments may be combined to form a yarn or they may be braided. In another example, filaments may be combined to form a yarn and then those multifilament yarns may be braided. Those skilled in the art reading this disclosure will envision other ways in which filaments may be combined. Fibers may also be combined to produce a non-woven multifilament large diameter suture. In certain embodiments, a multifilament structure useful in forming an anchoring suture according to the present disclosure may be produced by braiding. The braiding can be done by any method within the purview of those skilled in the art. For example, braid constructions for sutures and other medical devices are described in U.S. Pat. Nos. 5,019,093; 5,059,213; 5,133,738; 5,181,923; 5,226,912; 5,261,886; 5,306,289; 5,318,575; 5,370,031; 5,383,387; 5,662,682; 5,667,528; and 6,203,564; the entire disclosures of each of which are incorporated by reference herein. Furthermore, the anchoring device may include portions which are monofilament and portions which are multifilament. In some embodiments, the proximal end of the elongate body may be a multifilament and the looped portion (loop portion described below) may be a monofilament.

Additionally, the anchoring device may include biologically acceptable additives such as plasticizers, antioxidants, dyes, dilutants, bioactive agents and combinations thereof, which can be coated on the filaments or fibers, or impregnated into the fibers or filaments (e.g. during compounding or extrusion) used to form the anchoring suture of the present disclosure.

Bioactive agents, sometimes referred to herein as therapeutic agents, which may be added to anchoring devices in accordance with the present disclosure include, but are not limited to, drugs, amino acids, peptides, polypeptides, proteins, polysaccharides, muteins, immunoglobulins, antibodies, cytokines (e.g., lymphokines, monokines, chemokines), blood clotting factors, hemopoietic factors, interleukins (1 through 18), interferons ($\beta$-IFN, $\alpha$-IFN and $\gamma$-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone, luteinizing hormone releasing factor), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; cells, viruses, and ribozymes.

In embodiments, the therapeutic agent may include at least one of the following drugs, including combinations and alternative forms of the drugs such as alternative salt forms, free acid form, free base forms, pro-drugs and hydrates: analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate); antiasthmatics (e.g., ketotifen and traxanox); antibiotics (e.g., neomycin, streptomycin, chloramphenicol, cephalosporin, ampicillin, penicillin, tetracycline, and ciprofloxacin); antidepressants (e.g., nefopam, oxypertine, doxepin, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, and protriptyline); antidiabetics (e.g., biguanides and sulfonylurea derivatives); antifungal agents (e.g., griseofulvin, ketoconazole, itraconizole, amphotericin B, nystatin, and candicidin); antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine); anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone); antineoplastics (e.g., cyclophosphamide, actinomycin, bleomycin, dactinomycin, daunorubicin, doxorubicin, epirubicin, mitomycin, methotrexate, fluorouracil, gemcitabine, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, goserelin, leuprolide, tamoxifen, interferon alfa, retinoic acid (ATRA), nitrogen mustard alkylating agents, and piposulfan); antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene); immunosuppressive agents (e.g., cyclosporine, azathioprine, mizoribine, and FK506 (tacrolimus)); antimigraine agents (e.g., ergotamine, propanolol, isometheptene mucate, and dichloralphenazone); sedatives/hypnotics (e.g., barbiturates such as pentobarbital, pentobarbital, and secobarbital; and benzodiazapines such as flurazepam hydrochloride, triazolam, and midazolam); antianginal agents (e.g., beta-adrenergic blockers; calcium channel blockers such as nifedipine, and diltiazem; and nitrates such as nitroglycerin, isosorbide dinitrate, pentearythritol tetranitrate, and erythrityl tetranitrate); antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine); antimanic agents (e.g., lithium carbonate); antiarrhythmics (e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine); antiarthritic agents (e.g., phenylbutazone, sulindac, penicillanine, salsalate, piroxicam, azathioprine, indomethacin, meclofenamate, gold sodium thiomalate, ketoprofen, auranofin, aurothioglucose, and tolmetin sodium); antigout agents (e.g., colchicine, and allopurinol); anticoagulants (e.g., heparin, heparin sodium, and warfarin sodium); thrombolytic agents (e.g., urokinase, streptokinase, and alteplase); antifibrinolytic agents (e.g., aminocaproic acid); hemorheologic agents (e.g., pentoxifylline); antiplatelet agents (e.g., aspirin); anticonvulsants (e.g., valproic acid, divalproex sodium, phenytoin, phenytoin sodium, clonazepam, primidone, phenobarbitol, carbamazepine, amobarbital sodium, methsuximide, metharbital, mephobarbital, mephenytoin, phensuximide, paramethadione, ethotoin, phenacemide, secobarbitol sodium, clorazepate dipotassium, and trimethadione); antiparkinson agents (e.g., ethosuximide); antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, and); agents useful for calcium regulation (e.g., calcitonin, and parathyroid hormone); antibacterial agents (e.g., amikacin sulfate, aztreonam, chloramphenicol, chloramphenicol palirtate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antiviral agents (e.g., interferon alpha, beta or gamma, zidovudine, amantadine hydrochloride, ribavirin, and acyclovir); antimicrobials (e.g., cephalosporins such as cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin); anti-infectives (e.g., GM-CSF); bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; albuterol; flunisolide; fluticasone proprionate; steroidal compounds and hormones (e.g., androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium); hypoglycemic agents (e.g., human insulin, purified beef insulin, purified pork insulin, glyburide, chlorpropamide, glipizide, tolbutarnide, and tolazamide); hypolipidemic agents (e.g., clofibrate, dextrothyroxine sodium, probucol, pravastitin, atorvastatin, lovastatin, and niacin); proteins (e.g., DNase, alginase, superoxide dismutase, and lipase); nucleic acids (e.g., sense or anti-sense nucleic acids encoding any therapeutically useful protein, including any of the proteins described herein); agents useful for erythropoiesis stimulation (e.g., erythropoietin); antiulcer/antireflux agents (e.g., famotidine, cimetidine, and ranitidine hydrochloride); antinauseants/antiemetics (e.g., meclizine hydrochloride, nabilone, prochlorperazine, dimenhydrinate, promethazine hydrochloride, thiethylperazine, and scopolamine); as well as other drugs useful in the compositions and methods described herein include mitotane, halonitrosoureas, anthrocyclines, ellipticine, ceftriaxone, ketoconazole, ceftazidime, oxaprozin, albuterol, valacyclovir, urofollitropin, famciclovir, flutamide, enalapril, mefformin, itraconazole, buspirone, gabapentin, fosinopril, tramadol, acarbose, lorazepan, follitropin, glipizide, omeprazole, fluoxetine, lisinopril, tramsdol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecainid, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, verapamil, nabumetone, trovafloxacin, dolasetron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide. In some embodiments, the drug may be water soluble. In some embodiments, the drug may not be water soluble.

Methods for combining these therapeutic agents with compositions of the present disclosure are within the purview of those skilled in the art and include, but are not limited to mixing, blending, dipping, spraying, wicking, solvent evaporating and the like.

Various compositions and materials may also be applied to the anchoring sutures and/or pledgets or included in the filaments or fibers to improve mechanical properties such as handling and knot strength or to deliver medicinal agents. Suitable coating materials include any materials conventionally applied to sutures. For example, suitable materials include fatty acid esters which may be combined with the metal salt of a fatty acid in the coating composition. Such esters include, for example, calcium stearate, stearoyl lactylate esters, palmityl lactylate esters, oleyl lactylate esters such as calcium, magnesium, aluminum, barium, or zinc stearoyl lactylate, calcium, magnesium, aluminum, barium, or zinc palmityl lactylate; calcium, magnesium, aluminum, barium, or zinc oleyl lactylate; with calcium stearate and calcium stearoyl-2-lactylate (such as the calcium stearoyl-2-lactylate commercially available under the trade name VERV from American Ingredients Co., Kansas City, Mo.) being preferred. When desirable, the fatty acid ester may be combined with a solvent. Suitable solvents include polar and non-polar solvents including but not limited to alcohols (e.g., methanol, ethanol, propanol), chlorinated hydrocarbons (such as methylene chloride, chloroform, 1,2-dichloro-ethane), and aliphatic hydrocarbons such as hexane, heptene, ethyl acetate.

In embodiments, the anchoring device may be combined with and/or coated with suitable materials including polyalkylene oxides such as polyethylene oxide, polypropylene oxide, polyethylene glycol (PEG), polypropylene glycol, copolymers thereof, and the like, including those having acrylate groups such as acrylate PEGs, and acrylate PEG/PPG copolymers. Such combinations may include blends or copolymers with polyalkylene oxide oligomers or polymers or other non-toxic surfactants. The resulting composition may possess antimicrobial properties due to the presence of the copolymers described above. In other embodiments, the sutures may be combined with silicone acrylates. Coatings may be applied to the individual filaments or the anchoring suture at any time prior to sterilization techniques. Coatings can be applied to the filaments using any technique within the purview of those skilled in the art.

In the description that follows, the term "proximal" as used herein, means the portion of the device which is nearer to the user, while the term "distal" refers to the portion of the device which is further away from the user.

Sutures of the present disclosure include an elongate body, having both distal and proximal portions, the distal portion of which transitions from the elongate body to an anchoring loop. Methods for creating anchoring loops are within the purview of those skilled in the art and include but are not limited to welding, ultrasonic energy, cutting, molding and gluing. In preferred embodiments to be described later, the anchoring loop includes barbs along a surface.

Adjuncts to making loops, such as adhesives and glues, may also be employed in the anchoring suture. In some embodiments (FIGS. 1A, 1B), the distal portion of suture may be folded and fixed to elongate body using adhesives and glues. In alternate embodiments, as shown in FIGS. 2A and 2B, loop portion may initially be a separate component which connects to an elongate body and optionally glued in place. It should be understood that embodiments and methods described in FIGS. 1 and 2 can be used to create any of the anchoring suture embodiments described herein (FIGS. 3-6). Suitable materials such as absorbable and non-absorbable materials include, but not limited to cyanoacrylates, isocyanates, polyurethanes, polyamines, polyamides, polyacrylates, polymethacrylates, silicones, carbonates, and other synthetic monomers and polymers and combinations thereof.

Adhesives such as cyanoacrylates can be employed in creating sutures of the present disclosure. Suitable cyanoacrylates include materials derived from methyl cyanoacrylate, ethyl cyanoacrylate, butyl cyanoacrylate, octyl cyanoacrylate, isobutyl cyanoacrylate, and methoxypropyl cyanoacrylate and combinations thereof and the like.

The anchoring loop further includes barbs disposed along a surface. Barbs can be created on the anchoring suture using any technique, including but not limited to lasers, molding, knives, blades, stamping, and other cutting means within the purview of those skilled in the art. Ultrasonic energy can also be used to create barbs or barbs as described in U.S. Patent Application No. 60/994,173 filed on Sep. 17, 2007 entitled "Method of Forming Barbs on a Suture" the entire disclosures of which are incorporated by reference herein.

Figure 1B:
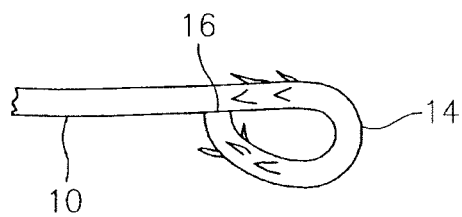
Figure 2A:
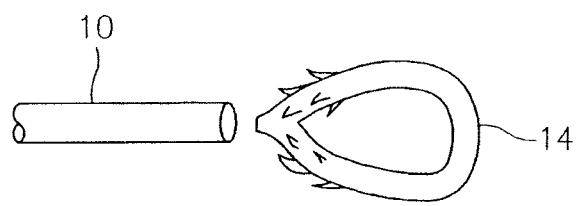
FIGS. 2A-2B are side views illustrating another embodiment of a looped suture.
Figure 2B:
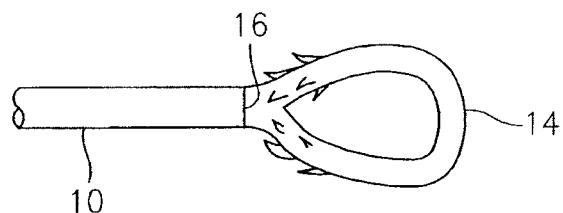
Figure 3:
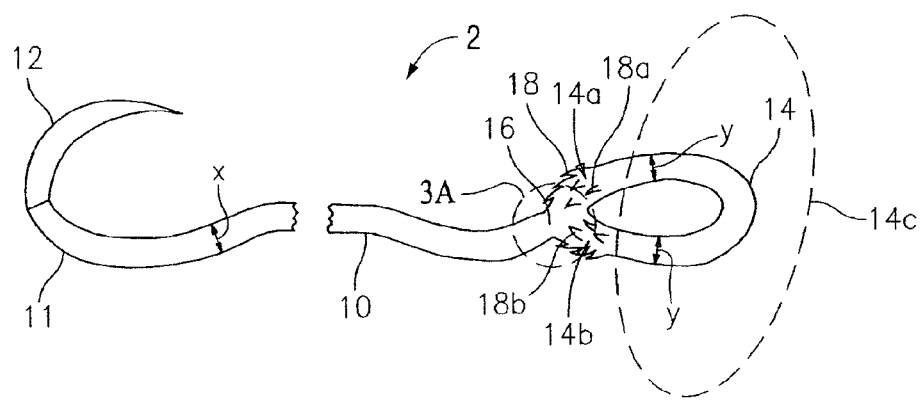
FIG. 3 is a side view illustrating one embodiment of an anchoring suture including barbs.

In some embodiments, anchoring sutures of the present disclosure include loops which are integral to an elongate body, as shown in FIGS. 1 and 3. Sutures with integral loops may be defined as having one structure or component in which the elongate body is continuous with the loop. For example, FIG. 1 shows an elongate body 10 in which the distal end is folded or "looped" to create a loop 14 (FIG. 1B) at the distal end of the medical device. The suture as shown in FIGS. 1 and 2 further includes transition area 16 and barbs which will be described in further detail below. An anchoring suture may also contain an integral loop as shown in FIG. 3, wherein the loop portion may be molded. In alternate embodiments, such as FIG. 2, anchoring sutures may comprise two components which are fixed or fitted together in a fashion as to create the anchoring suture. For example, the elongate body 10 may include a female component while the loop 14 may include a male component and the two components may be fitted together to create a final product. One skilled in the art can envision other manufacturing processes in which to create integral loops and medical devices with integral and non-integral loops.

Figure 3A:
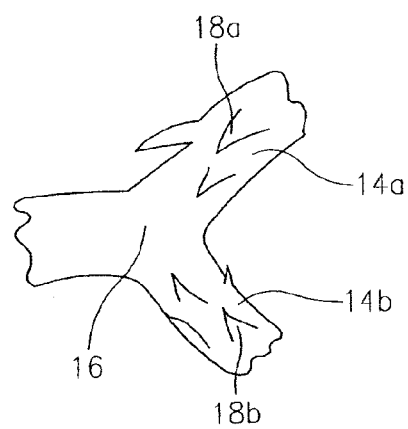
FIG. 3A is an enlarged view of the area of detail designated in FIG. 3.

Another embodiment of the anchoring suture of the present disclosure is shown in FIG. 3 and is designated generally by reference numeral 2. Suture 2 has an elongate body 10, a proximal portion of elongate body 10 terminating in a free end 11, and a distal portion of the elongate body 10 which forms, transitions into, or terminates in a loop 14. As shown in FIG. 3, the free end 11 further comprises a needle 12. The elongate body 10 has a diameter "x" and, in preferred embodiments, the elongate body 10 is generally elliptical in transverse cross-section. The distal end of elongate body 10 extends into a loop 14, bifurcating at transition area 16 (FIGS. 3 and 3A). Loop 14 includes two branches 14a and 14b, which may be identical in shape and cross-sectional area, to both each other and elongate body 10. In preferred embodiments, sections 14a and 14b are generally elliptical in shape and cross-sectional area, although other shapes are envisioned such as circular, oval, square, and rectangular. In the embodiment shown in FIG. 3, the loop 14 may be integral with the elongate body 10 of the suture 2. In alternate embodiments, the loop 14 may be a separate component prior to assembly (FIGS. 1 and 2), and during assembly the loop 14 may be attached to the elongate body 10. The loop 14 has a generally arcuate surface, and each branch (14a and 14b) has an independent diameter "y", of which 14a and 14b may be of similar or different diameters. The loop may be of any shape including circular, oval, polygonal.

Furthermore, anchoring suture of FIG. 3 includes a first plurality of barbs 18 disposed along a surface of the loop 14. Barbs 18a are disposed along surface of branch 14a and barbs 18b are disposed along branch 14b. Additionally, segment 14c is used to designate a loop segment in which barbs are absent. In the illustrated embodiment, barbs 18 are located adjacent transition area 16 of elongate body 10 and anchoring loop 14. Furthermore, the first plurality of barbs 18 is oriented such that movement of the anchoring loop 14 towards the proximal end is limited. As shown in FIG. 3, barbs 18 are oriented towards transition area 16 to prevent movement of anchoring loop 14 through tissue. In embodiments shown, barbs 18 are integral to the anchoring loop 14.

Figure 4A:
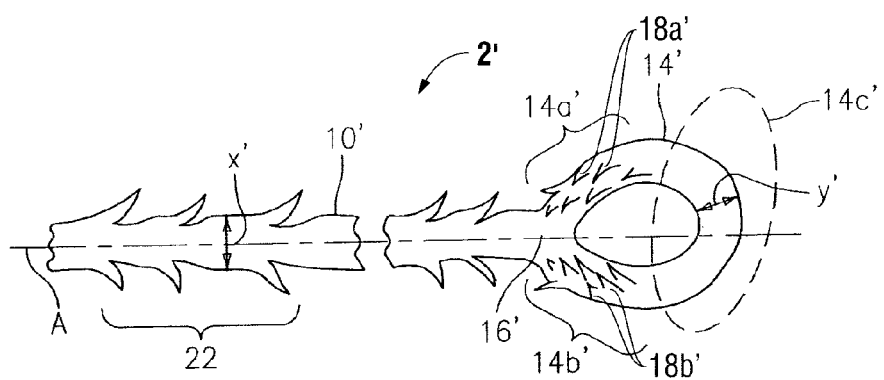
FIG. 4A is a side view illustrating an alternate embodiment of an anchoring suture including barbs.

It will be understood that FIG. 4A is a generally similar to FIG. 3 and therefore all numerals and descriptions which are the same in FIG. 3 are designated with the prime mark and have some differences. FIG. 4A shows an alternate embodiment of an anchoring suture 2' in which a second plurality of barbs 22 is disposed along the elongate body 10'. The second plurality of barbs 22 extends in the second direction which is different from a first direction of the first plurality of barbs. In the embodiment shown, the first plurality of barbs 18' are disposed along a loop surface and extend in the first direction, generally towards transition area 16' of the anchoring suture 2'. The second plurality of barbs 22 extend in a second direction, towards the loop 14', with respect to longitudinal axis A of the elongate body 10.

Figure 4B:
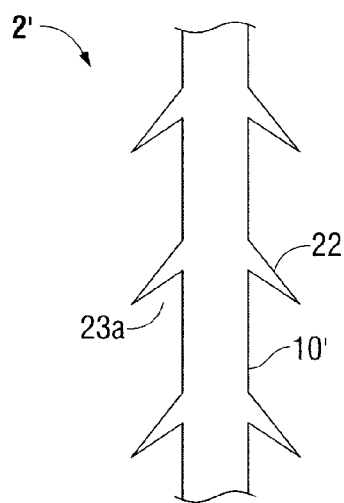
FIG. 4B is a plan view of a portion of a barbed medical device having shape memory polymer barbs in a permanent configuration in accordance with an embodiment of the present disclosure.
Figure 4C:
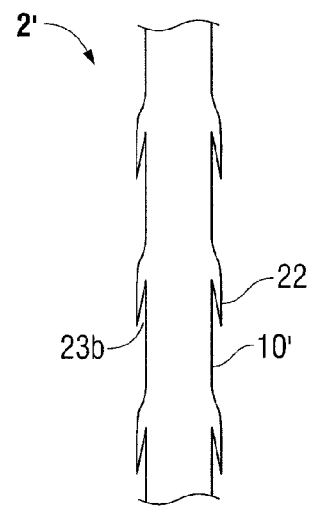
FIG. 4C is a plan view of a portion of a barbed medical device having shape memory polymer barbs in a temporary configuration in accordance with an embodiment of the present disclosure.

In embodiments, the first set of barbs 18' and/or second plurality of barbs 22 may be made of shape memory polymers. As depicted in FIG. 4B, barb 22 extends outwardly and away from elongate body 10' thereby forming an barb angle 23a between barb 22 and elongate body 10' of anchoring suture 2'. The suture may then be deformed into a temporary shape, as illustrated in FIG. 4C, in which the barbs 22 are pressed against the elongate body 10' and the barb angles 23b are smaller than the barb barbs 23a of the permanent shape, e.g., closed. As illustrated in FIG. 4C, in the temporary shape, barbs 22 are substantially parallel to the longitudinal axis of the elongate body 10' of suture 2' to from barb angle 23b. Upon placement in the tissue the barbs 22 may extend away from the elongate body 10' back to their permanent shape as depicted in FIG. 4B.

Figure 5:
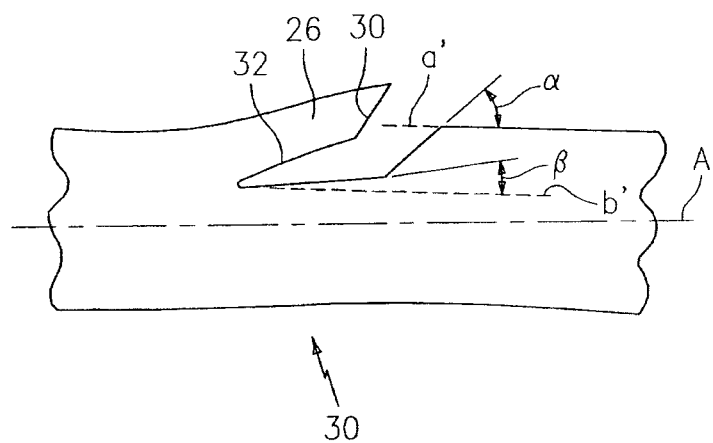
FIG. 5 is an enlarged side view showing an alternate embodiment of an anchoring suture having a compound barb.

In the alternate embodiment shown in FIG. 5, anchoring suture 30 includes a compound barb 26 having an inner surface 30 including a first angle $\alpha$, disposed at a first orientation relative to a longitudinal axis "A'" of the elongate body and a second angle $\beta$ having a second inner surface 32, disposed at a second orientation relative to a longitudinal axis b of the elongate body. The anchoring suture may optionally include a third orientation (not shown). In the embodiment shown, the first, second and third orientations are each disposed at different angles with respect to the longitudinal axis. In some embodiments, the anchoring suture may include a staggered arrangement of large or small barbs. In other embodiments, an anchoring suture may have a random configuration of both large and small barbs. It will be understood that the embodiment shown in FIG. 5 is generally similar to FIGS. 3 and 4A, but has a different geometry for the barbs. In alternate embodiments, the above-mentioned compound barb geometry may also be present on the anchoring loop (not shown).

The surface area of the plurality of barbs can also vary. For example, fuller-tipped barbs can be made of varying sizes designed for specific surgical applications. When joining fat and relatively soft tissues, larger barbs may be desired, whereas smaller barbs may be more suitable for collagen-dense tissues. In some embodiments (FIG. 4A), a combination of large and small barbs within the same structure may be beneficial, for example when a fiber is used in tissue repair with differing layer structures. Use of the combination of large and small barbs with the same fiber wherein barb sizes are customized for each tissue layer will ensure maximum holding properties.

Figure 6:
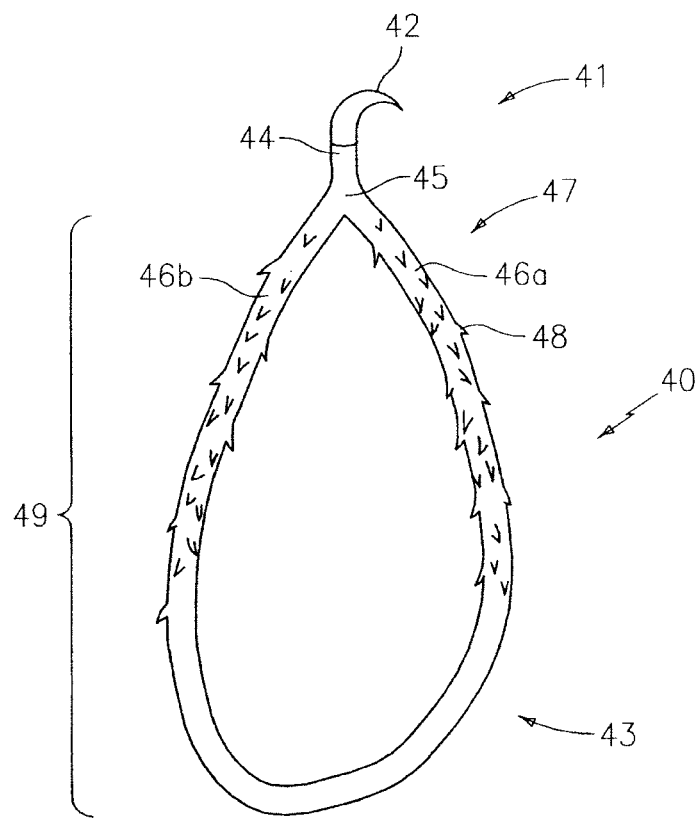
FIG. 6 is a side view illustrating another embodiment of an anchoring suture including barbs.

Another embodiment of an anchoring device is shown in FIG. 6. The anchoring device 40 includes a needle 42 at a proximal end 41 of the device. The device bifurcates at a transition area 45, and a distal portion of the device terminates in an anchoring loop 49. The anchoring loop 49 includes two branches 46a and 46b at a proximal end 47 of the anchoring loop 49. The anchoring loop 49 has a generally arcuate surface, branches 46a and 46b may have similar or different diameters. In the illustrated embodiment, a first plurality of barbs 48 are located adjacent the transition area 45. Furthermore, the first plurality of barbs 48 is oriented such that movement of the anchoring loop 49 in tissue, in a direction towards the distal end 43 of the device, is limited. As illustrated in FIG. 6, the device may have an elongate body 44 that is shorter in longitudinal length as compared to the anchoring loop 49. The two branches of the loop may be advanced through a single needle penetration point and pulled through tissue; the method of which will be described in detail later.

Figure 7:
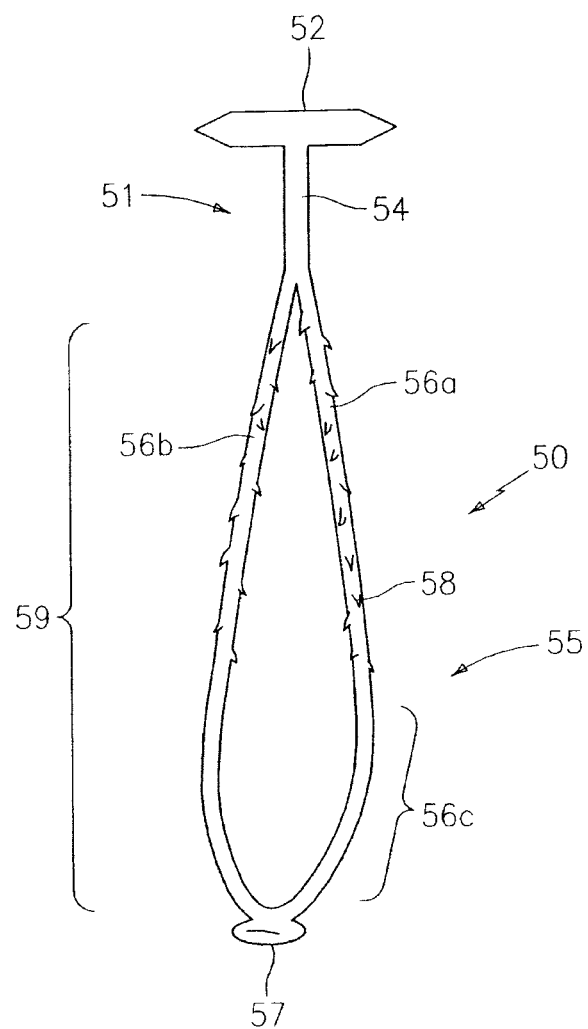
FIG. 7 is a side view illustrating an alternate embodiment of an anchoring suture with an end effector.

FIG. 7 illustrates an alternate embodiment of an anchoring device 50 which may be used in combination with a mechanical suturing device such as an Endo Stitch™ suturing device commercially available from Tyco Healthcare Group LP. Anchoring device 50 includes a needle 52 which is compatible with a mechanical suturing device such as an Endo Stitch™ suturing device. The proximal portion 51 of the anchoring suture includes an elongate body 54, and the distal portion 55 of the suture terminates in a loop 59. The loop 59 includes two branches 56a and 56b and each branch includes a plurality of barbs 58 on a surface thereof. In other embodiments, a plurality of barbs may only be on a surface of at least one branch or a portion of the anchoring device. The loop 59 also includes an unbarbed distal portion 56c. The loop further includes an end effector 57 which limits movement of the anchoring device through tissue. In some embodiments, the end effector is located on the unbarbed distal portion 56*c* of the loop (FIG. 7). As illustrated, the end effector 57 is a bulk (large mass) of suture material, which is generally "T"-shaped and in the current embodiment, the end effector is welded to the loop 59.

Figure 8C:
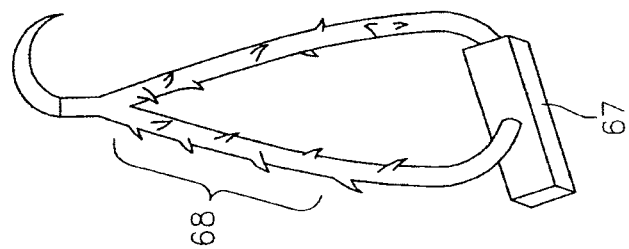
FIG. 8C is a side view of an alternate embodiment of an anchoring suture with an end effector.
Figure 8B:
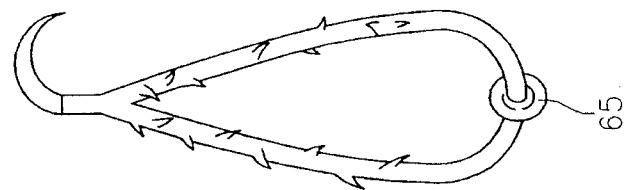
FIG. 8B is a side view of a different embodiment of an anchoring suture with an end effector.
Figure 8A:
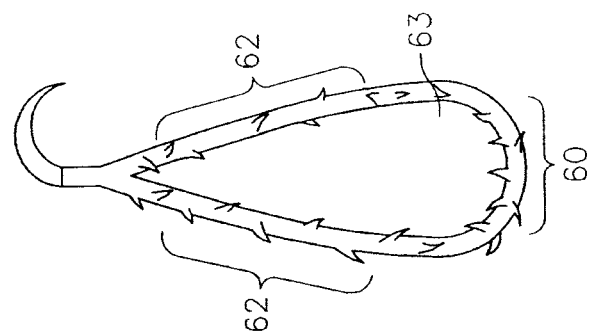
FIG. 8A is a side view of another embodiment of an anchoring suture with an end effector.

This disclosure contemplates different end effectors and non-limiting alternate embodiments are illustrated in FIGS. 8A, 8B and 8C. In FIG. 8A an end effector is illustrated as a second plurality of barbs 60 which are oriented such that movement of an end portion of the loop 63 through tissue towards a proximal end of the anchoring suture is limited. In this embodiment, a first plurality of barbs 62 located at a proximal portion of the loop 63 are shown oriented in a generally opposite direction to a second plurality of barbs 60, which are located at a distal portion of loop 63. In another embodiment, FIG. 8B, the end effector is a bead 65 of a polymeric material. In some embodiments, the bead may of a similar material to the anchoring loop and in alternate embodiments; the bead may be comprised of a different material than the anchoring loop. In some embodiments, such as FIGS. 8A and 8B, the end effector is integral with the loop. In yet other embodiments, the end effector may be a separate device such as a pledget or buttress. As illustrated in FIG. 8C, the end effector is a pledget 67 formed on or otherwise attached to the loop. In this embodiment, prior to creating a loop, a suture may penetrate the pledget 67 and a length of the suture may be pulled through the pledget. It should be noted that once the pledget has been moved across a portion of barbs 68 projecting from the suture surface, the barbs will prevent the pledget from disengaging the suture and the barbs will retain the pledget in place on the suture. Next, a loop may be created via various means including those described above, and the pledget 67 may be positioned at a distal most point of the anchoring loop. It should be understood that end effectors are not limited to those structures described herein and one skilled in the art may contemplate other shapes and devices which may be used for a similar purpose. End effectors may be constructed using methods within the purview of those skilled in the art, including but not limited to glues, adhesives, lasers, ultrasonic or heat welding, molding, overmolding and the like. Any of the suture materials and structures discussed above may be used to form the anchoring devices discussed herein.

The pledget may be integral with, for example co-formed, or separate from the suture. If the pledget is separate from the suture, the pledget may be placed over the needle and elongate body prior to use.

As used herein, the term "tissue" includes, but is not limited to, tissues such as skin, fat, fascia, bones, muscles, tendons, ligaments, organs, nerves, and blood vessels. Also used herein, the term "wound" includes, but is not limited to, a surgical incision, cut, laceration or severed tissue in human or animal skin or other human or animal bodily tissue.

Figure 9A:
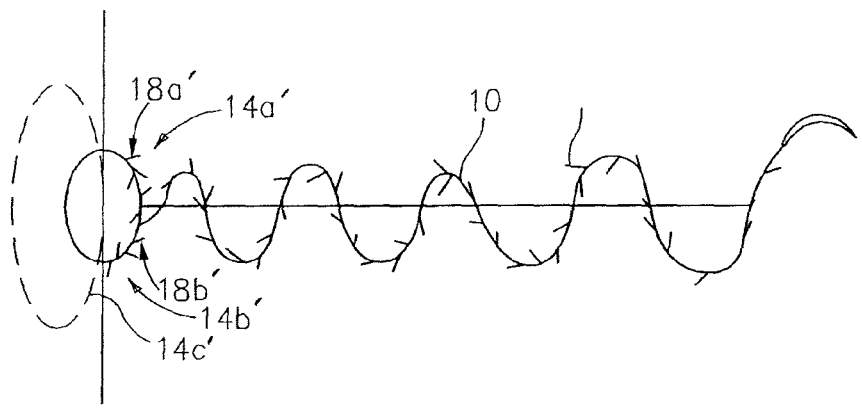
FIG. 9A is a plan view of the anchoring suture of FIG. 4A in tissue with portions of tissue removed.
Figure 9B:
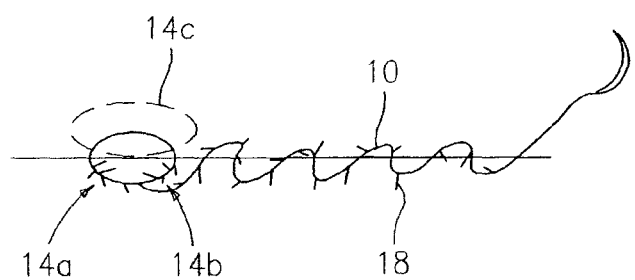
FIG. 9B is a side view of the anchoring suture of FIG. 4A in tissue with portions of tissue removed.

Tissue may be sutured by inserting proximal portion of an anchoring suture into tissue at a first section and advancing the proximal portion of the suture through a second section of the tissue, and exiting tissue at an exit point. The suture is pulled through the exit point until the first plurality of barbs on the anchoring loop engages tissue and resists movement in direction of needle advancement, thus preventing further advancement of anchoring loop through tissue. The proximal portion of the suture may optionally be inserted through the segment of the loop remaining outside the body tissue for enhanced fixation. FIGS. 9A and 9B show the embodiment of FIG. 4A, where an unbarbed loop segment 14*c'* remains exterior to the wound site (or external to skin in dermal closure) due to the barbs 18*a'* and 18*b"* and lack of barbs on segment 14*c**. It should be understood that all embodiments described herein can be used in a similar fashion. Upon exit of tissue, needle and proximal end of suture may be passed through segment of loop which remains exterior to wound site to secure suture in place. User may then continue suturing wound, entering and exiting tissue until wound site is closed (or implant attached).

Figure 10A:
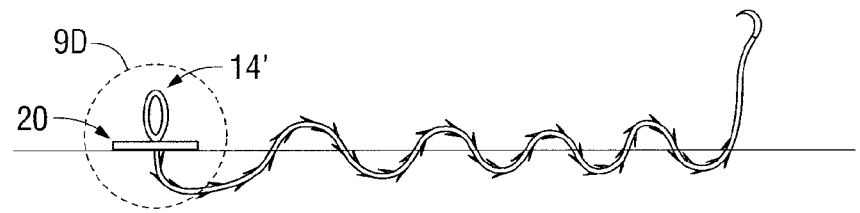
FIG. 10A is a side view of an alternate embodiment anchoring suture in tissue with portions of tissue removed.
Figure 10B:
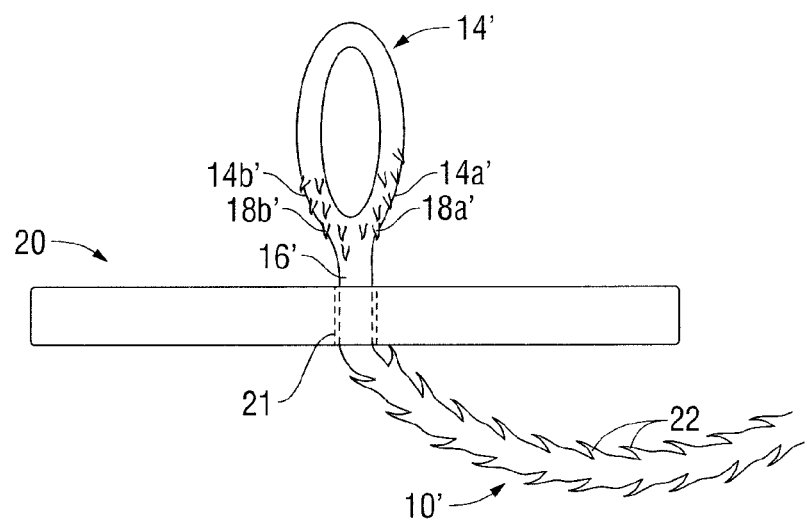
FIG. 10B is an enlarged view of the area of detail designated in FIG. 10A.

In one embodiment, tissue may be sutured by inserting the proximal portion of an anchoring suture into tissue at a first section and advancing the proximal portion of the suture through a second section of the tissue, and exiting tissue at an exit point. The suture is pulled through the exit point until the pledget engages tissue and the barbed portion of the loop resists movement of the pledget in direction of needle advancement, thus preventing further advancement of the pledget and anchoring loop through tissue. The pledget may broaden the anchoring capability of the suture by distributing the stress placed on the suture across a broader area and thereby enhancing suture capability in situations where the suture is likely to be exposed to a high level of tension. The proximal portion of the suture may optionally be inserted through the segment of the loop remaining outside the body tissue for enhanced fixation. FIG. 10A illustrates the suture of FIG. 4A, where a pledget 20 is positioned at the distal end of elongate portion 10 and adjacent the proximal end of loop 14. FIG. 10B illustrates an enlarged section of the loop 14 and pledget 20. (The loop is still present, to start a running stitch without tying a knot at the end; the pledget anchors the suture at the distal end to prevent pull through and stabilize the distal end.)

Figure 11A:
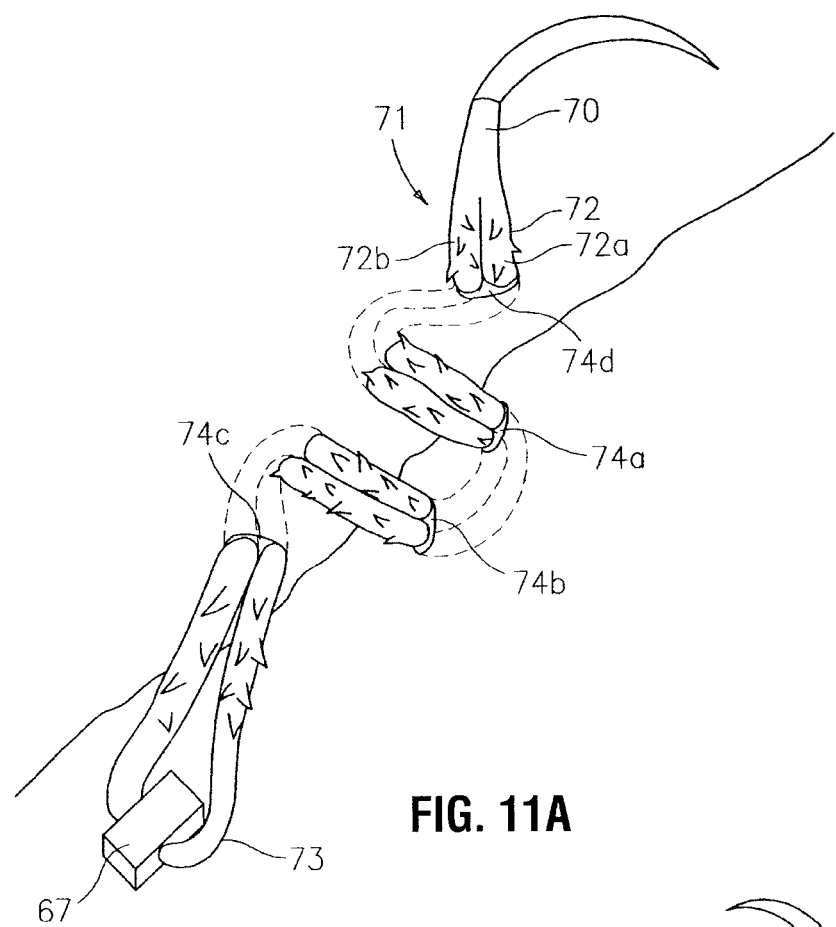
FIG. 11A is a plan view of the anchoring suture of FIG. 8C in a first position in tissue, with portions of tissue removed.
Figure 11B:
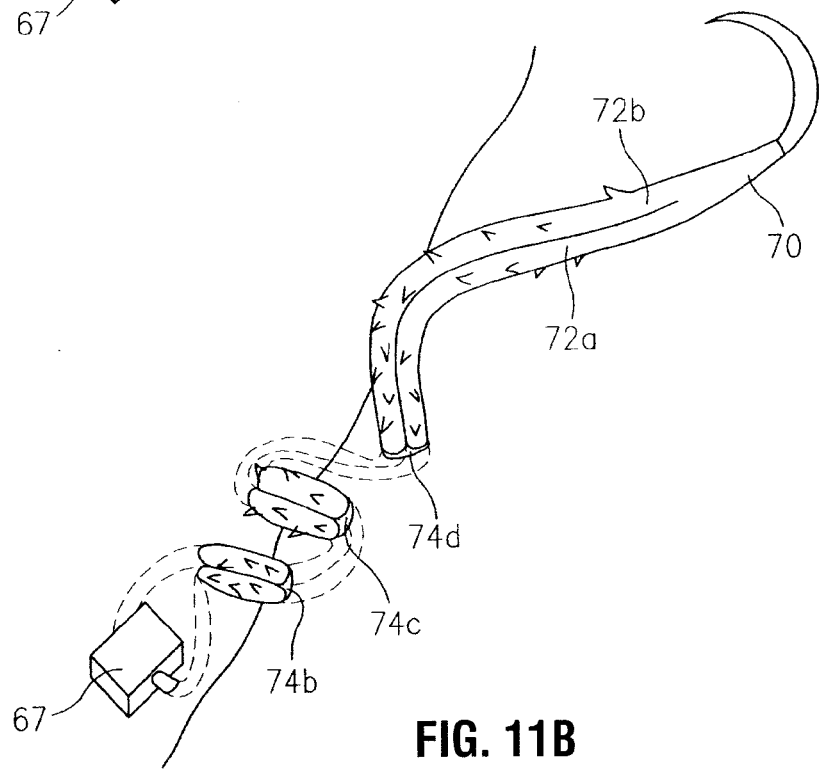
FIG. 11B is a plan view of the anchoring suture of FIG. 8C in a second position in tissue, with portions of tissue removed.

FIGS. 11A and 11B illustrate the embodiment of FIG. 8C in tissue. Tissue may be secured in a similar manner as described above, by inserting a proximal portion of the anchoring device into tissue at a first section and advancing the proximal portion of the anchoring device, including a proximal portion of the loop, through a second section of the tissue, and exiting tissue at an exit point. In the embodiments described in FIGS. 6, 7, 8A, 8B, and 8C once the needle is advanced through tissue, the remainder of the suture follows including the two branches of the loop. More specifically, the two branches of the loop are advanced through a needle penetration point (or points through which the needle and elongate body have passed). FIG. 11A illustrates a first position of the embodiment of an anchoring device as described in FIG. 8C. As illustrated, proximal portion of suture 70 and proximal portion 71 of loop 72, including two branches 72*a* and 72*b*, are advanced through tissue. Both branches 72*a* and 72*b* are advanced through needle penetration points (74*a*, 74*b*, 74*c*, and 74*d*), the barbs engage tissue and suture holding force is increased. FIG. 11B shows the embodiment of FIG. 8C in a second position. Once the anchoring suture has been further advanced through tissue, the pledget 67 prevents any further movement of the distal loop portion through tissue. It should be understood that other embodiments of end effectors and shown and described would function in a manner similar to the embodiment described with respect to FIGS. 11A and 11B. It should also be understood that anchoring sutures without end effectors may also be inserted and advanced through tissue in a similar manner.

Figure 12A:
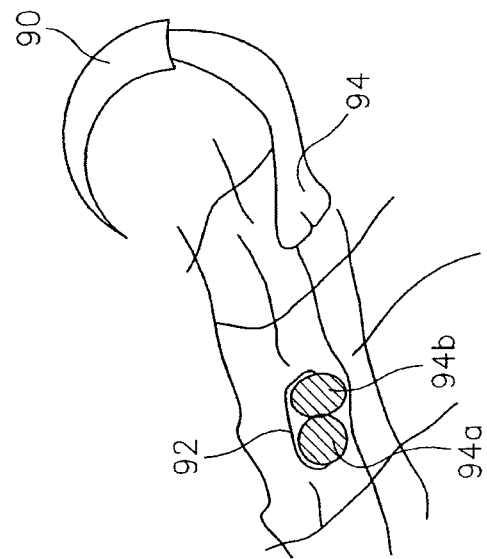
FIG. 12A shows a perspective view, partially in cross-section, of a suture filling a needle penetration point; and, FIG. 12B shows a perspective view, partially in cross-section, of an anchoring suture of the present disclosure filling a needle penetration point.
Figure 12B:
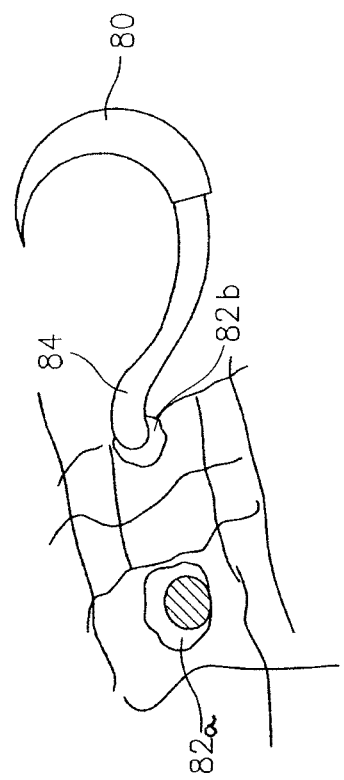

FIG. 12A shows the prior art in which an oversized needle 80 penetrates tissue, and leaves a tissue penetration point (82*a* and 82*b*) that a single suture strand 84 may not fill. FIG. 12B shows one embodiment of the current disclosure in which an oversized needle 90 penetrates tissue and the two branches (94*a* and 94*b*) of the anchoring device 94 can better fill the needle penetration point 92. The two branches of the loop in combination with the barbs allow an increase in tissue holding strength which may be desirable in certain applications.

In order to facilitate needle attachment to an anchoring suture or device of the present disclosure, conventional tipping agents can be applied to the braid. Two tipped ends of the fiber may be desirable for attaching a needle to each end of the fiber to provide a so-called double armed suture. The needle attachment can be made by any conventional method such as crimping, swaging, etc, as is known within the purview of those skilled in the art. Alternatively, a reduced diameter may be provided at the end of the suture to be inserted into the drilled end of a needle. To provide a reduced diameter, the suture may by machined using any technique within the purview of those skilled in the art, such as cutting, grinding, laser machining or the like.

Anchoring devices, including anchoring sutures of the present disclosure may be employed in medical devices, drug delivery devices and cell growth substrates. Examples of suitable medical devices and/or surgical devices employing the anchoring sutures may include, but are not limited to meshes, wound dressings, bandages, drug delivery devices, anastomosis rings, stents, grafts, catheter systems, soft tissue repair and augmentation devices, scaffolds, buttresses, lap bands, tapes, barbs, ribbons, orthopedic devices, tissue engineering scaffolds, various cell growth substrates, and other implantable devices. In some embodiments, devices of the present disclosure may be knitted or woven with other fibers, either absorbable or non-absorbable, to form surgical devices. The anchoring devices and/or sutures also can be made into meshes or non-woven materials to form fabrics, such as matted fabrics and felts.

Additionally, anchoring devices of the present disclosure may be packaged using materials known to those within the purview of those skilled in the art, including foil and various plastics (e.g. polyethylene), which may provide a moisture barrier. Once the anchoring device is constructed, it can be sterilized by any means within the purview of those skilled in the art including but not limited to ethylene oxide, electron beam (e-beam), gamma irradiation, autoclaving, and the like.

Example 1

Distal end of MAXON™ suture is folded towards elongate body to create a loop, and suture (loop) is then placed in an ultrasonic welding apparatus, where loop is welded closed. Suture is then affixed to an ultrasonic cutting apparatus to create barbs. Elongate body and anchoring loop of anchoring suture is cut via ultrasonic blades at various angles.

Example 2

Distal end of SURGIPRO™ suture is folded towards elongate body to create loop and glue is placed on elongate body and distal suture end is folded over and attached to elongate body, creating a fixed loop. Suture is then affixed to a cutting apparatus and anchoring suture is cut at various angles using a knife. Anchoring suture is then coated with a chemotherapeutic agent using solvent casting.

Example 3

Distal end of MAXON™ suture is folded towards elongate body to create a loop, and suture (loop) is then placed in an ultrasonic welding apparatus, where loop is welded closed. The ultrasonic welding apparatus is then used to weld a distal end of the loop into a generally "T"-shape, creating an end effector. Suture is next affixed to an ultrasonic cutting apparatus to create barbs. Elongate body and a proximal portion of the anchoring loop of anchoring suture is cut via ultrasonic blades at various angles.

Example 4

Distal end of MAXON™ suture is folded towards elongate body to create a loop, and suture (loop) is then placed in an ultrasonic welding apparatus, where loop is welded closed. Suture is then affixed to an ultrasonic cutting apparatus to create barbs. Elongate body and anchoring loop of anchoring suture is cut via ultrasonic blades at various angles. A 3 mm polyester disc having a central opening is then advanced over the needle and elongate body of the suture and placed in abutment with the proximal portion of the loop.

It should be noted that the present disclosure is not limited to wound closure and contemplates other procedures such as cosmetic and orthopedic procedures. Additionally, the above description contains many specifics; these specifics should not be construed as limitations on the scope of the disclosure herein but merely as exemplifications of particularly useful embodiments thereof. Those skilled in the art will envision many other possibilities within the scope and spirit of the disclosure as defined by the claims appended hereto.

What is claimed is:

1. A medical device comprising:
an elongate body having a proximal portion and a distal portion, the proximal portion of the elongate body terminating in a free end and the distal portion of the elongate body including a loop and a first plurality of barbs extending towards the proximal portion along a surface of the loop; and
a pledget disposed about the elongate body proximal of the loop,
wherein at least one of the loop or the barbs comprises a shape memory polymer configured to change shape in vivo upon application of energy.

2. The medical device of claim 1, wherein the pledget comprises a polymer selected from the group consisting of polylactide, polyglycolide, polycaprolactone, polydioxanone, poly(trimethylene carbonate), and copolymers and combinations thereof.

3. The medical device of claim 1, wherein the elongate body comprises a polymer selected from the group consisting of polylactide, polyglycolide, polycaprolactone, polydioxanone, poly(trimethylene carbonate), and copolymers and combinations thereof.

4. The medical device of claim 1, wherein the pledget comprises a copolymer comprising from about 55% to about 65% by weight glycolide, from about 10% to about 18% by weight dioxanone, and from about 17% to about 35% by weight trimethylene carbonate.

5. The medical device of claim 1, wherein the elongate body comprises a copolymer comprising from about 55% to about 65% by weight glycolide, from about 10% to about 18% by weight dioxanone, and from about 17% to about 35% by weight trimethylene carbonate.

6. The medical device of claim 1, wherein the pledget comprises a copolymer comprising from about 60% to about 75% by weight glycolide and from about 25% to about 40% by weight trimethylene carbonate.

7. The medical device of claim 1, wherein the elongate body comprises a copolymer comprising from about 60% to about 75% by weight glycolide and from about 25% to about 40% by weight trimethylene carbonate.

8. The medical device of claim 1, wherein the pledget comprises a copolymer comprising butylene terephthalate and polytetramethylene ether glycol.

9. The medical device of claim 1, wherein the elongate body comprises a copolymer comprising butylene terephthalate and polytetramethylene ether glycol.

10. The medical device of claim 1, wherein the pledget and the elongate body are each formed of materials which degrade within a period of from about 0 days to about 180 days after placement in a patient.

11. The medical device of claim 1, wherein the pledget and the elongate body each lose structural integrity within a period of from about 90 days to about 110 days after placement in a patient.

12. The medical device of claim 1, wherein the shape memory polymer is selected from the group consisting of bioabsorbable materials, non-degradable materials, and combinations thereof.

13. The medical device of claim 1, wherein the shape memory polymer comprises a non-degradable material selected from the group consisting of polyolefins, polyethylene glycols, polyethylene oxides, polyolefin copolymers, fluorinated polyolefins, polyamides, polyamines, polyimines, polyesters, polyethers, polybutesters, polyurethanes, acrylic polymers, methacrylics polymers, vinyl halide polymers and copolymers, polyvinyl alcohols, polyvinyl ethers, polyvinylidene halides, polychlorofluoroethylene, polyacrylonitrile, polyaryletherketones, polyvinyl ketones, polyvinyl aromatics, polyvinyl esters, copolymers of vinyl monomers, acrylonitrile-styrene copolymers, ABS resins, ethylene-vinyl acetate copolymers, alkyd resins, polycarbonates, polyoxymethylenes, polyphosphazines, polyimides, epoxy resins, aramids, rayons, spandex, silicones, and combinations thereof.

14. The medical device of claim 1, wherein the shape memory polymer comprises a bioabsorbable material selected from the group consisting of aliphatic polyesters, polyamides, polyamines, polyalkylene oxalates, poly(anhydrides), polyamidoesters, copoly(ether-esters), poly(carbonates), poly(hydroxyalkanoates), polyimide carbonates, poly (imino carbonates), polyorthoesters, polyoxaesters, polyphosphazenes, poly (propylene fumarates), polyurethanes, polymer drugs, biologically modified bioabsorbable polymers, and copolymers, homopolymers, and combinations thereof.

15. The medical device of claim 1, wherein the shape memory polymer comprises an aliphatic polyester selected from the group consisting of homopolymers and copolymers of lactide, glycolide, epsilon-caprolactone, p-dioxanone, trimethylene carbonate, alkyl derivatives of trimethylene carbonate, Δ-valerolactone, β-butyrolactone, γ-butyrolactone, δ-decalactone, hydroxybutyrate, hydroxyvalerate, 1,4-dioxepan-2-one, 1,5-dioxepan-2-one, 6,6-dimethyl-1,4-dioxan-2-one, 2,5-diketomorpholine, pivalolactone, α,α diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one, and combinations thereof.

16. The medical device of claim 1, wherein the shape memory polymer comprises a biodegradable polymer selected from the group consisting of poly(amino acids), collagen, elastin, fibrin, fibrinogen, silk, albumin, peptides including sequences for laminin and fibronectin, hyaluronic acid, dextran, alginate, chitin, chitosan, cellulose, glycosaminoglycan, gut, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, nitrocelluloses, chitosan, and combinations thereof.

17. The medical device of claim 1, wherein the shape memory polymer comprises a polymer selected from the group consisting of oligo (epsilon-caprolactone) dimethacrylates, oligo (epsilon-caprolactone) butyl acrylates, (n-butyl acrylate), oligo (epsilon caprolactone) diol/oligo (p-dioxanone) diol copolymers, polycaprolactone dimethacrylate poly(butyl acrylate) blends, and combinations thereof.

18. The medical device of claim 1, wherein the shape memory polymer comprises a block copolymer of polydioxanone and polylactide.

19. The medical device of claim 18, wherein the polydioxanone is present in an amount from about 15 mol % to about 20 mol % of the copolymer and the polylactide is present in an amount from about 80 mol % to about 85 mol % of the copolymer.

20. The medical device of claim 1, wherein the shape memory polymer comprises a block copolymer of trimethylene carbonate and polylactide.

21. The medical device of claim 20, wherein the trimethylene carbonate is present in an amount from about 5 mol % to about 20 mol % of the copolymer and the polylactide is present in an amount from about 80 mol % to about 95 mol % of the copolymer.

22. The medical device of claim 1, further comprising a therapeutic agent.

23. The medical device of claim 1, wherein the medical device comprises a non-degradable material selected from the group consisting of polyolefins, polyethylene glycols, polyethylene, fluorinated polyolefins, polyamides, vinyl halide polymers, and copolymers, homopolymers, blends, and combinations thereof.

24. The medical device of claim 1, wherein the pledget limits movement of at least a portion of the loop through tissue such that a segment of the loop remains outside a body tissue.

25. The medical device of claim 1, wherein the pledget engages tissue to prevent movement of the loop in a proximal direction.

26. The medical device of claim 1, further comprising a needle secured to the free end of the proximal portion of the elongate body.

27. The medical device of claim 1, wherein the pledget is disposed in abutment with the proximal portion of the loop.

28. The medical device of claim 1, further comprising a second plurality of barbs disposed along the elongate body, wherein the second plurality of barbs comprise the shape memory polymer and are configured to have a temporary shape in which the barbs are pressed against the elongate body and a permanent shape in which the barbs extend outwardly and away from the elongate body, thereby forming a barb angle between the barbs and the elongate body.

29. The medical device of claim 1, wherein the first plurality of barbs are oriented toward the proximal portion of the elongate body to limit movement of the loop through tissue.

30. The medical device of claim 1, wherein the first plurality of barbs are disposed on a proximal portion of the loop, and a distal portion of the loop is free of barbs.

31. A medical device comprising:
  an elongate body having a proximal portion and a distal portion, the proximal portion of the elongate body terminating in a free end and the distal portion of the elongate body including a loop and a first plurality of barbs disposed along an outer surface of the loop extending towards the proximal portion of the elongate body; and a pledget disposed about the elongate body between the free end and the distal portion.

* * * * *